United States Patent [19]

Park

[11] Patent Number: 5,300,287

[45] Date of Patent: Apr. 5, 1994

[54] POLYMERIC ANTIMICROBIALS AND THEIR USE IN PHARMACEUTICAL COMPOSITIONS

[75] Inventor: Joonsup Park, Arlington, Tex.

[73] Assignee: Alcon Laboratories, Inc., Fort Worth, Tex.

[21] Appl. No.: 971,424

[22] Filed: Nov. 4, 1992

[51] Int. Cl.$^5$ .......................................... A61K 31/785
[52] U.S. Cl. ........................... 424/78.04; 424/78.35; 514/840; 526/304; 526/307.2; 528/422; 528/423; 528/424
[58] Field of Search ................ 424/405, 78.04, 78.35, 424/78.74; 528/422, 423, 424; 526/307.2, 304

[56] References Cited

U.S. PATENT DOCUMENTS

| | | |
|---|---|---|
| 3,539,684 | 11/1970 | Hoover .......................... 424/78.35 |
| 3,778,476 | 12/1973 | Rembaum et al. . |
| 3,898,336 | 8/1975 | Rembaum et al. . |
| 3,931,319 | 1/1976 | Green et al. . |
| 4,001,432 | 1/1977 | Green et al. . |
| 4,012,446 | 3/1977 | Green et al. . |
| 4,032,293 | 6/1977 | Perrier et al. . |
| 4,250,269 | 2/1981 | Buckman et al. . |
| 4,499,077 | 2/1985 | Stockel et al. . |
| 4,654,208 | 3/1987 | Stockel et al. . |
| 4,836,986 | 6/1989 | Ogunbiyi . |
| 5,104,649 | 4/1992 | Jansson et al. . |
| 5,120,809 | 6/1992 | Lupo et al. ...................... 424/307.2 |
| 5,171,526 | 12/1992 | Wong et al. ...................... 424/78.04 |

FOREIGN PATENT DOCUMENTS

WO91/09522  7/1991  PCT Int'l Appl. .
WO91/09523  7/1991  PCT Int'l Appl. .
1556365  11/1979  United Kingdom .

*Primary Examiner*—Thurman K. Page
*Assistant Examiner*—Peter F. Kulkosky
*Attorney, Agent, or Firm*—Julie J. L. Cheng

[57] ABSTRACT

Novel polymeric antimicrobials having spacer moieties between amine and/or ammonium moieties have good antifungal activity. These compounds are useful in pharmaceutical and cosmetic compositions as preservatives and in contact lens care compositions as preservatives and/or disinfectants.

22 Claims, No Drawings

POLYMERIC ANTIMICROBIALS AND THEIR USE IN PHARMACEUTICAL COMPOSITIONS

BACKGROUND OF THE INVENTION

The present invention relates generally to a novel class of polymeric compounds which are useful as antimicrobials in pharmaceutical and cosmetic compositions. In particular, the present invention relates to novel polymeric compounds having spacer moieties in between amine and/or ammonium moieties. The compounds of the present invention are useful as disinfectants and preservatives for pharmaceutical products, including ophthalmic compositions and contact lens care products.

It is well known that small organic compounds, such as benzalkonium chloride (BAC), chlorhexidine, thimerosal have excellent antimicrobial activity. These compounds have been commercially used as preservatives and disinfectants for many years; however, there are some significant disadvantages to using these compounds, especially in ophthalmic and contact lens compositions. In particular, it is now known that these small organic antimicrobials are often toxic to the sensitive tissues of the eye and can accumulate in contact lenses, particularly soft, hydrophilic contact lenses. Accumulation of these antimicrobial compounds in contact lenses may cause eye irritation, and leaching of such compounds may occur while the lens is in the eye, causing further irritation and possibly damaging the cornea.

Several classes of polymeric antimicrobials were subsequently developed to overcome the disadvantages of the above-described monomeric compounds. These polymeric antimicrobials had lower cytotoxicity and had minimal interaction with biomaterials. Such antimicrobials include those described in U.S. Pat. No. 3,931,319 (Jan. 6, 1976), U.S. Pat. No. 4,001,432 (Jan. 4, 1977) and U.S. Pat. No. 4,012,446 (Mar. 15, 1977), all issued to Green, et al. and U.S. Pat. No. 4,836,986 (Jun. 6, 1989), issued to Ogunbiyi. Although these polymeric antimicrobials exhibit a broad spectrum of antimicrobial activity, including activity against *Candida albicans* and *Pseudononas aeruginosa*, the above-described polymeric antimicrobials generally have relatively weak antifungal activity, especially against *Aspergillus niger* and *Aspergillus fumigates*.

Second generation polymeric antimicrobials have since been developed, including those described in the following publications: WO 91/09522 (Wong et al.) and WO 91/09523 (Dziabo et al.). The antimicrobials disclosed in Wong et al. are quaternary ammonium-substituted matrix materials, wherein the matrix material is selected from proteinaceous materials, carbohydrate materials or mixtures thereof. Dziabo et al. disclose certain quaternary ammonium polymers which are useful as ophthalmic antimicrobials.

SUMMARY OF THE INVENTION

For purposes of this specification, disinfectants and/or preservatives shall be collectively referred to as "antimicrobials" and compounds having disinfecting and/or preserving efficacy shall be referred to as compounds having "antimicrobial activity."

It has now been found that certain novel polymeric compounds exhibit good, broad spectrum antimicrobial activity, including good antifungal activity, and have low toxicity. These novel polymeric compounds may be generally described as containing "fingers" extending from a polymeric backbone, wherein the "fingers" consist of polyethylene glycol (PEG) moieties ("spacers") in between amine and/or ammonium moieties and the polymeric backbone may consist of: homo- and copolymers of $-(CH_2)_n-$ alkenes, such as poly(methacrylate), poly(acrylate) and poly(styrene); polyamines; polyimines; and other polymeric backbones.

The ophthalmic compositions of the present invention comprise the polymers of the present invention. These compositions include: contact lens care products, such as chemical disinfecting and storage solutions and preserved saline solutions; and other types of ophthalmic compositions, such as artificial tears and topical pharmaceutical preparations.

DETAILED DESCRIPTION OF THE INVENTION

Preferred polymers of the present invention are the random copolymers of Structure (I), below:

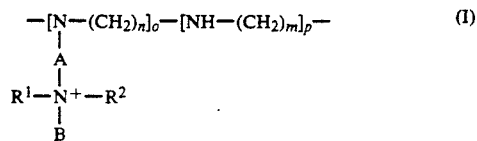

(I)

and pharmaceutically acceptable salts thereof, wherein:

n and m can be the same or different and are: integers between 1 and 10;

$o+p=z$, wherein z is the total number of structural units and z is a number between 3 and 10,000, preferably a number between 3 and 100 and most preferably a number between 20 and 50, and wherein o is a fraction of z between 0 and 100% and p is a fraction of z between 100 and 0%;

$R^1$ and $R^2$ can be the same or different and are $C_1$-$C_5$ alkyl;

B can be substituted or unsubstituted, branched or unbranched: $C_1$-$C_{30}$ alkyl, $C_1$-$C_{24}$ alkyl-substituted benzyl, $C_3$-$C_{15}$ alkyl silane, or $C_6$-$C_{15}$ cycloalkyl or arylalkyl; and A can be substituted or unsubstituted, branched or unbranched: $C_1$-$C_{20}$ alkyl, cycloalkyl, alkyleneoxy, heteroatom-containing spacers, such as succinimide and succinate esters.

Also preferred are the random copolymers of Structure (II), below:

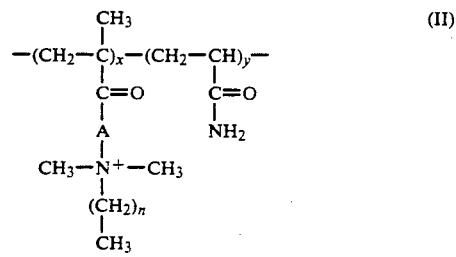

(II)

and pharmaceutically acceptable salts thereof, wherein:

A can be substituted or unsubstituted, branched or unbranched: $C_1$-$C_{20}$ alkyl, cycloalkyl, alkyleneoxy, or a heteroatom-containing spacer moiety;

$x+y=W$, wherein w is the total number of structural units and w is a number between 3 and 1,000, preferably a number between 3 and 100 and most preferably a number between 20 and 50, and wherein x is a fraction of w between 0 and 100% and y is a fraction of w between 100 and 0%; and n is an integer between 5 and 30.

The random copolymers of Structures (I) and (II) may be synthesized according to the following general synthetic procedures.

1. Preparation of a compound of Structure (I)

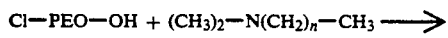

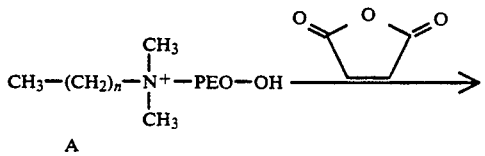

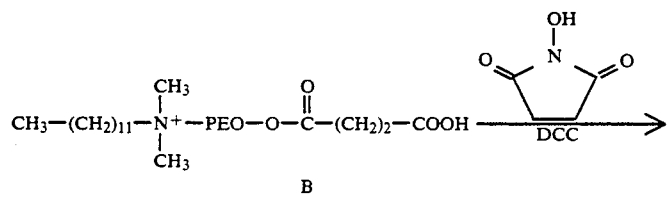

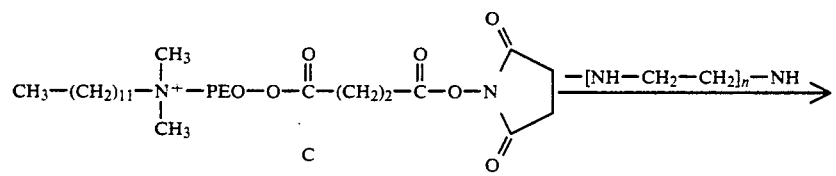

Compound of Structure (I)

The starting material (Cl-PEO-OH) is commercially available from Aldrich (Milwaukee, Wis.). This is reacted with N,N-dimethyldodecylamine to afford Compound A. Succinic anhydride is reacted with Compound A to make the corresponding hemi-ester (Compound B), which is then activated by n-hydroxysuccinimide to form the activated ester (Compound C). Compound C is then reacted with polyethyleneimine to obtain the modified polymer product.

2. Alternative preparation of a compound of Structure (I)

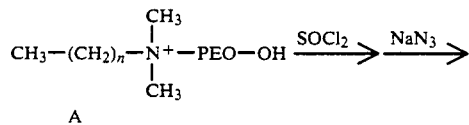

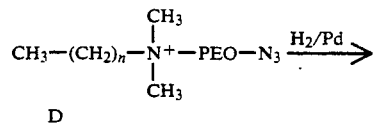

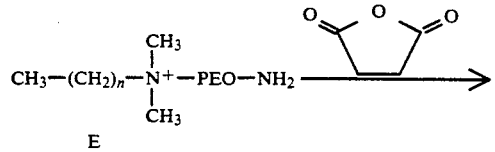

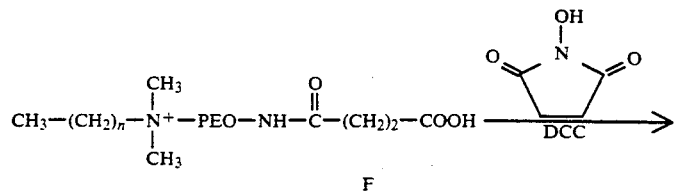

Equation 2

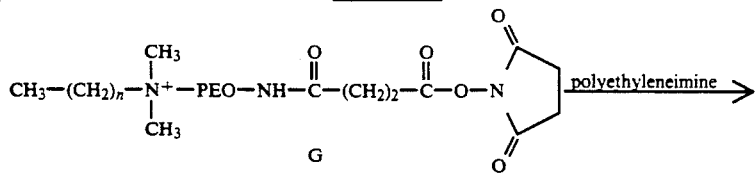

Compound of Structure (I)

Compound A is converted to the corresponding chloro compound, which is reacted with sodium azide to afford azido compound (D). Compound D is reduced by hydrogenation to the corresponding amino compound (E) which is reacted with succinic anhydride to afford compound F. This is then activated by N-hydroxysuccinimide to afford compound G. This activated ester (Compound G) is reacted with polyethyleneimine to obtain the modified polymers of Structure (I).

3. Preparation of a compound of Structure (II)

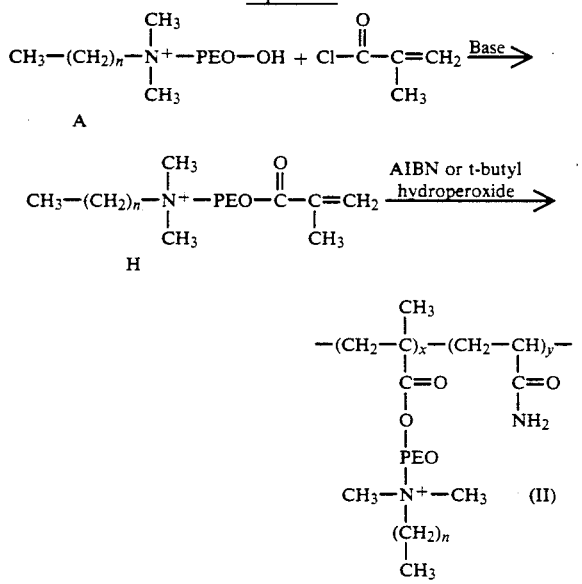

Compounds of Structure (II) may be synthesized by utilizing one of the intermediates (Compound A) for the synthesis of Structure (I). Compound A is reacted with methacryloyl chloride in the presence of base to afford Compound H. Compound H is then polymerized in the presence of an appropriate initiator, such as AIBN (α,α-azobisisobutyronitrile) or tert-butyl hydroperoxide. Copolymerization has also been performed with an appropriate monomer such as acrylamide, by utilizing the same procedure as described above.

The polymers of the present invention may be used as antimicrobials in ophthalmic compositions, particularly as disinfectants in contact lens care products and as preservatives in other types of ophthalmic compositions, such as artificial tears or topical pharmaceutical preparations. In general, the polymers of the present invention will be present in the compositions at a concentration between about 0.00001 and 1.0 percent by weight (wt %). If used as a disinfectant, the polymers are preferably present at a concentration of between about 0.0005 and 0.5 wt %; if use as a preservative, the polymers are present at a concentration between about 0.00005 and 0.05 wt %. It is preferred that the polymers are present at a concentration of between 0.001 and 0.05 wt % if used as a disinfectant and between 0.0001 and 0.01 wt % if used as a preservative.

The ophthalmic compositions of the present invention may additionally contain other components, for example, ophthalmically acceptable buffers, tonicity agents, surfactants and therapeutic agents.

The following Examples 1-3 illustrate the synthesis of several of the polymers of the present invention.

EXAMPLE 1: Synthesis of AL04385A

2-[2-(2-Chloroethoxy)ethoxy]ethanol, 3.36 grams ("g") (0.02 moles "mol")) was reacted with 4.08 g (0.02 mol) of N,N-dimethyldodecylamine at 125° C. for 5 hours, and then the reaction mixture was triturated with ethyl acetate 5 times to afford a white powder. Yield was 7.3 g (96%). Nuclear magnetic resonance (3.5 ppm for N+CH$_3$; 1.2 ppm for the alkyl chain) and infrared spectroscopy (3400 cm$^{-1}$(OH), 1120 cm$^{-1}$(PEO), 1090 cm$^{-1}$(OH)) confirmed the structure.

The above product (7.6 g, 0.02 mol) was reacted with 2.2 g (0.022 mol) of succinic anhydride and 1.8 g (0.022 mol) of pyridine in 60 milliliters ("mL") of dry chloroform (distilled over P$_2$O$_5$) under reflux for 5 hours. This mixture was then washed with saturated NaCl and hydrochloric acid until the pH of aqueous layer was about 2.0, evaporated in vacuo, and triturated with ethyl acetate to afford semi-solid compounds. Yield was 9.0 g (93.7%). NMR spectrum showed N+CH$_3$ at 3.35 ppm, CH$_2$CH$_2$C at 2.65 ppm, and the long alkyl chain at 1.3 ppm.

The above acid (9.6 g, 0.02 mol) was reacted with 2.3 g (0.02 mol) of N-hydroxysuccinimide and 4.5 g (0.22 mol) of DCC in dry chloroform on the ice bath for 5 hours. The precipitate was filtered and the filtrate was dissolved in ethyl acetate and kept in the refrigerator overnight. The crystalline precipitate was then filtered and the filtrate evaporated in vacuo to yield 11 g (95%). This process was repeated two times. NMR spectrum confirmed the structure: 2.9 ppm for succinimide; 2.95 ppm and 2.8 ppm (two sets of triplets) for —CCH$_2$CH$_2$CO. IR spectrum also indicated the existence of the activated ester at 1810, 1770, 1730 (cm$^{-1}$).

The above activated ester (5.78 g, 0.01 mol) was reacted with 0.43 g (0.01 mol) of polyethyleneimine (molecular weight 1200, available from Polysciences, Warrington, Pa.) in dry chloroform on the ice bath for one hour, and at room temperature for another 5 hours. This reaction mixture was washed with saturated NaCl solution for 5 times and evaporated in vacuo to leave 4.3 g of yellowish material. This was subjected to a molecular weight 6000-8000 cut off membrane and dialyzed twice against water. The dialyzed material was lyophilized to leave very hygroscopic materials.

Elemental analysis: Calculated for 40% modification with ⅔ water: C=57.78; H=10.34: N=8.13. Found: C=57.90; H=9.9; N=8.45. IR spectra indicated the existence of amide (1640 cm$^{-1}$) and ester (1720 cm$^1$) moieties.

EXAMPLE 2: Synthesis of Compound I

2-[2-(2-chloroethoxy)ethoxy]ethanol (12.18 g, 0.072 mol) was reacted with 17.4 g (0.072 mol) of N,N-dimethyltetradecylamine at 125° C. with stirring for 6 hrs and the product (Compound A) was crystallized from ethylacetate. (m.p.=66°–68° C.; 72% yield).

Compound A (15.0 g, 0.037 mol) was chlorinated with 8.9 g of thionyl chloride (0.073 mol) and 5.8 g (0.073 mol) of pyridine in chloroform solution under reflux. This chlorinated compound was purified by washing successively with saturated NaCl solution, saturated NaCl/Na$_2$CO$_3$ solution, and saturated NaCl solution. Yield was 15.46 g (96%). This was converted to the azido derivative with NaN$_3$ in DMF at 85° C. for 75 minutes. The reaction mixture was then washed with saturated NaCl solution (75 mL×6) and concentrated in vacuo to leave compound D.

IR: 2120 cm$^{-1}$ (CN) NMR (CDCl$_3$)δ: 3.41 (s, 8H, NCH$_3$ and RCH$_2$), 1.3 (broad s, 22H, (CH$_2$)$_{11}$CH$_3$)).

Compound D (15 g, 0.034 mol) was hydrogenated in ethanol with 3.4 g of 10% Pd/C at 10 psi afforded 13.4 g (94%) of compound E.

NMR (CDCl$_3$)δ: 3.41 (s, 6H, NCH$_3$); 2.88 (t, 2H, RCH$_2$NH$_2$);1.3 (broad s, 22H, (CH$_2$)$_{11}$CH$_3$))

Compound E (13.36 g, 0.034 mol) was reacted with 3.40 g (0.034 mol) of succinic anhydride in chloroform with 1.4 g of triethylamine. The reaction mixture was stirred at room temperature overnight, washed with acidic solution of saturated sodium chloride and dried over MgSO$_4$. This was concentrated in vacuo to leave a viscous material which was dissolved in chloroform and precipitated with ethylacetate.

IR: 1735 cm$^{-1}$ and 1670 cm$^{-1}$ acid and amide, respectively. NMR (CDCl$_3$)δ: 2.6 (m, 4H, COCH$_2$CH$_2$) 1.3 (broad s, 22H, (CH$_2$)$_{11}$CH$_3$)). Elemental analysis: calcd. for C$_{26}$H$_{53}$ClN$_2$O$_5$: C=61.33; H=10.49; N=5.50. Found: C=61.46; H=10.55; N=5.28.

Compound F (10.78 g, 0.02 mol) was coupled with 2.5 g of N-hydroxy succinimide (0.022 mol) and 4.5 g of dicyclohexylcarbodiimide (0.022 mol) in chloroform to form Compound G.

IR: 1820 and 1790 cm$^{-1}$ for anhydride. NMR (CDCl$_3$) δ: 3.36 (s, 6H, N-CH$_3$) 2.87 (s, 4H, succinimide), 1.3 (broad s, 22H), 0.09 (t, 3H, CH$_3$).

Compound G (7.04 g, 0.017 mol) was reacted with 0.27 g of polyethyleneimine (molecular weight 1200, purchased from Polysciences) in chloroform in an ice bath for an hour. This reaction mixture was washed with saturated NaCl solution (3×75 ml) and evaporated in vacuo to leave a glassy material which was dialyzed four times against water with a membrane having a cutoff of molecular weight 1000. This was then dried by lyophilization to leave 2.6 g (28%) of a glassy, yellow polymeric material.

Elemental analysis: calcd. (based on 33% modification) for C$_{32}$H$_{66}$ClN$_5$O$_4$ (+2.3 H$_2$O): C=58.04; H=10.81; N=10.58. Found: C=57.84; H=10.56; N=10.91. IR: 1600 cm$^{-1}$ for amide. NMR (CDCl$_3$) δ: 3.38 (s, NCH$_3$), 1.3 (broad s, (CH$_2$)$_{11}$CH$_3$)).

EXAMPLE 3: Synthesis of Compound II

Compound A (3.81 g, 0.01 mol) was reacted with 1.05 g (0.01 mol) of methacryloyl chloride and 1.5 g (0.015) mol of triethylamine in the presence of DPQ (2,5-diphenyl benzoquinone) (100 ppm) in 30 mL of chloroform. This reaction mixture was stirred at room temperature for 5 hrs and washed with saturated NaCl solution four times and dried over MgSO$_4$. This was concentrated in vacuo to leave a viscous material which was dissolved in chloroform and precipitated with n-hexane. This process was repeated three times and the precipitate then dried under high vacuum.

NMR (CDCl$_3$) δ: 6.0 and 5.5 (app. 2d, 2H, CH=); 3.25 (s, 6H, NCH$_3$); 1.85 (s, 3H, CH$_2$=C—CH$_3$). Elemental analysis: calcd. for C$_{23}$H$_{48}$ ClNO$_4$ (438.09): C=63.06; H=10.96; N=3.19. Found: C=62.99; H=11.20; N=2.93.

Acrylamide (0.158 g, 2.2 mmol) was copolymerized with 1.0 g of Compound H (2.2 mmol) in the presence of 0.16 g of 2-mercaptoethanol (0.37 mmol). Freshly distilled (over lithium aluminum hydride) tetrahydrofuran (THF) was used as a solvent and one drop of USP-245 was employed as an initiator. The reaction mixture was flushed with argon for 10 minutes and polymerized at 55°–65° C. for four hours. Polymer was isolated by precipitation method with water-dioxane and dried in vacuo.

NMR (D$_2$O) δ: 3.1 (s, 6H, N-CH$_3$);1.2 (broad s, NCH$_2$(CH$_2$)$_9$—); No vinylic protons were observed from nmr spectrum. Elemental analysis: calcd. for (Acrylamide)$_3$(Compound H)$_2$ C$_{57}$H$_{111}$N$_5$O$_{11}$Cl$_2$ (+1.8 H$_2$O): C=59.73; H=10.10; N=6.11. Found: C=59.765; H=10.04; N=5.92.

EXAMPLE 4

Some compounds of the present invention were evaluated for preservative activity using an abbreviated method according to the criteria for USP, BP, DAB preservative efficacy tests. The polymeric compounds, plus BAC as a control, were prepared as 0.01% solutions in a vehicle containing 3% mannitol and 0.1% NaCl in 5 mL Hepes buffer. The vehicle was also used as a control. The microorganisms tested were *A. niger, P. aeruginosa,* and *S. aureus.* The results are shown in the following Table 1.

TABLE 1

| | LOG REDUCTION | | | | | | | |
|---|---|---|---|---|---|---|---|---|
| | 6 Hours | | 24 Hours | | | Day 7 | | |
| | S.a. | P.a. | S.a. | P.a. | A.n. | S.a. | P.a. | A.n. |
| AL04385A (0.01%) | 5.2 | 5.2 | 5.9 | 5.9 | 3.8 | 5.2 | 5.2 | 5.3 |
| AL04437A (0.01%) | 5.3 | 5.1 | 6.0 | 5.8 | 2.1 | 5.3 | 5.1 | 3.5 |
| Al04384A (0.01%) | 5.2 | 5.2 | 5.9 | 5.9 | 0.7 | 5.2 | 5.2 | 5.3 |
| PEI (0.01%) | 5.3 | 5.1 | 6.0 | 5.8 | 0.1 | 5.3 | 5.1 | 0.6 |
| Polyquad ® (0.01%) | 5.3 | 5.1 | 6.0 | 5.8 | 0.0 | 5.3 | 5.1 | 0.7 |
| BAC (0.001%) | 5.3 | 5.1 | 6.0 | 5.8 | 1.9 | 5.3 | 5.1 | 2.2 |
| Vehicle | 0.5 | 1.3 | 0.6 | 0.7 | 0.6 | 1.7 | 0.0 | 0.7 |

The invention has been described by reference to certain preferred embodiments; however, it should be understood that it may be embodied in other specific forms or variations thereof without departing from its spirit or essential characteristics. The embodiments described above are therefore considered to be illustra-

What is claimed is:

1. A random co-polymer of formula:

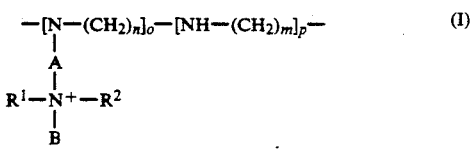

and pharmaceutically acceptable salts thereof, wherein:
n and m can be the same or different and are: integers between 1 and 10;
o+p=z, wherein z is the total number of structural units and z is a number between 3 and 10,000, and wherein o is a fraction of z between 0 and 100% and p is a fraction of z between 100 and 0%;
$R^1$ and $R^2$ can be the same or different and are selected from the group consisting of $C_1$-$C_5$ alkyl;
B can be substituted or unsubstituted, branched or unbranched and is selected from the group consisting of: $C_1$-$C_{30}$ alkyl, $C_1$-$C_{24}$ alkyl-substituted benzyl, $C_3$-$C_{15}$ alkyl silane, and $C_6$-$C_{15}$ cycloalkyl or arylalkyl; and
A can be substituted or unsubstituted, branched or unbranched and is selected from the group consisting of: $C_1$-$C_{20}$ alkyleneoxy.

2. The random co-polymer of claim 1, wherein: n=m=2; z is a number between 3 and 100; $R^1$=$R^2$=$C_1$-$C_2$ alkyl; and B=substituted or unsubstituted, branched or unbranched $C_{12}C_{18}$ alkyl.

3. The random co-polymer of claim 2, wherein: n=m=2; z is a number between 20 and 50; $R^1$=$R^2$=$CH_3$; B=substituted or unsubstituted, branched or unbranched $C_{14}$ alkyl; and A=polyethyleneoxide succinate.

4. A random co-polymer of formula:

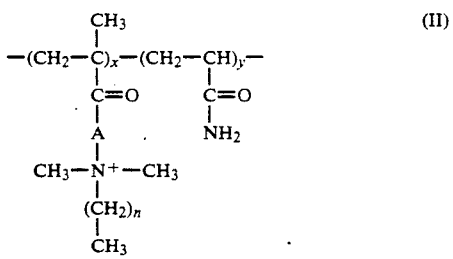

and pharmaceutically acceptable salts thereof, wherein:
A can be substituted or unsubstituted, branched or unbranched and is selected from the group consisting of: $C_1$-$C_{20}$ alkyleneoxy;
x+y=w, wherein w is the total number of structural units and w is a number between 3 and 1,000, and wherein x is a fraction of w between 0 and 100% and y is a fraction of w between 100 and 0%; and
n is an integer between 5 and 30.

5. The random co-polymer of claim 4, wherein: w is a number between 3 and 100; and n is an integer between 12 and 18.

6. The random co-polymer of claim 5, wherein: A=polyethylene oxide; w is a number between 20 and 50; and n=14.

7. A pharmaceutical composition comprising an antimicrobially effective amount of a random co-polymer of claim 1.

8. The composition of claim 7, wherein the random copolymer of claim 1 is present at a concentration between about 0.00001 and about 1.0 wt %.

9. The composition of claim 8, wherein the random copolymer of claim 1 is present at a concentration between about 0.0005 and about 0.5 wt %.

10. The composition of claim 9, wherein the random copolymer of claim 1 is present at a concentration between about 0.001 and about 0.05 wt %.

11. The composition of claim 8, wherein the random copolymer of claim 1 is present at a concentration between about 0.00005 and about 0.05 wt %.

12. The composition of claim 11, wherein the random copolymer of claim 1 is present at a concentration between about 0.0001 and about 0.01 wt %.

13. A pharmaceutical composition comprising an antimicrobially effective amount of a random copolymer of claim 4.

14. The composition of claim 13, wherein the random copolymer of claim 4 is present at a concentration between about 0.00001 and about 1.0 wt %.

15. The composition of claim 14, wherein the random copolymer of claim 4 is present at a concentration between about 0.0005 and about 0.5 wt %.

16. The composition of claim 15, wherein the random copolymer of claim 4 is present at a concentration between about 0.001 and about 0.05 wt %.

17. The composition of claim 14, wherein the random copolymer of claim 4 is present at a concentration between about 0.00005 and about 0.05 wt %.

18. The composition of claim 17, wherein the random copolymer of claim 4 is present at a concentration between about 0.0001 and about 0.01 wt %.

19. A method of disinfecting a contact lens, comprising contacting a contact lens to a composition comprising a disinfecting amount of a random copolymer of claim 1 for a time sufficient to disinfect the lens.

20. The method of claim 19, wherein the random copolymer of claim 1 is present at a concentration between about 0.00001 and about 1.0 wt %.

21. A method of disinfecting a contact lens, comprising contacting a contact lens to a composition comprising a disinfecting amount of a random copolymer of claim 4 for a time sufficient to disinfect the lens.

22. The method of claim 21, wherein the random copolymer of claim 4 is present at a concentration between about 0.00001 and about 1.0 wt %.

* * * * *